United States Patent
Mathieu et al.

(10) Patent No.: US 9,271,771 B2
(45) Date of Patent: Mar. 1, 2016

(54) DEVICE FOR OSTEOSYNTHESIS

(75) Inventors: Claude Mathieu, Zurich (CH); Robert Frigg, Bettlach (CH); Rolf Schneider, Port (CH); Andreas Appenzeller, Biel (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 2356 days.

(21) Appl. No.: 11/147,140

(22) Filed: Jun. 6, 2005

(65) Prior Publication Data

US 2006/0058797 A1    Mar. 16, 2006

Related U.S. Application Data

(63) Continuation of application No. PCT/CH02/00673, filed on Dec. 6, 2002.

(51) Int. Cl.
*A61B 17/80* (2006.01)

(52) U.S. Cl.
CPC ................... *A61B 17/8047* (2013.01)

(58) Field of Classification Search
CPC .................................................. A61B 17/8047
USPC .......... 248/586–587, 623, 626; 403/229, 372; 606/63, 66, 269, 288–294, 305; 411/16, 17, 21, 438, 929; 29/240.5, 29/456
See application file for complete search history.

(56) References Cited

U.S. PATENT DOCUMENTS

| | | | | |
|---|---|---|---|---|
| 388,000 A | * | 8/1888 | Rider | 411/399 |
| 548,085 A | * | 10/1895 | Palmer | 267/288 |
| 2,363,663 A | * | 11/1944 | Findley | 411/423 |
| 2,672,070 A | * | 3/1954 | Forster | 411/438 |
| 2,801,631 A | | 8/1957 | Charnley | |
| 3,033,622 A | * | 5/1962 | Renner | 384/537 |
| 3,316,795 A | * | 5/1967 | Tann | 411/17 |
| 3,435,526 A | * | 4/1969 | Brancato | 433/174 |
| 3,867,972 A | | 2/1975 | Gonzalez | |
| 4,004,486 A | * | 1/1977 | Schenk | 411/16 |
| 5,531,746 A | * | 7/1996 | Errico et al. | 606/287 |
| 5,860,779 A | * | 1/1999 | Toosky et al. | 411/432 |
| 6,213,775 B1 | * | 4/2001 | Reipur | 433/173 |
| 6,235,033 B1 | | 5/2001 | Brace et al. | |
| 6,358,250 B1 | * | 3/2002 | Orbay | 606/86 B |

(Continued)

FOREIGN PATENT DOCUMENTS

| | | |
|---|---|---|
| DE | 197 20782 | 11/1998 |
| EP | 0337288 | 10/1989 |

(Continued)

*Primary Examiner* — David Bates
(74) *Attorney, Agent, or Firm* — Fay Kaplun & Marcin, LLP

(57) ABSTRACT

A device of performing osteosynthesis includes an osteosynthesis element, e.g., a bone plate, having an upper face, a lower face and an opening with a central axis linking the upper and lower faces. The opening receives a multi-axial pivotable insert for a longitudinal bone fixing element, such as a bone screw. The insert has a central passage with a longitudinal axis for housing the bone fixing element. The insert may be configured as a helical spring with an external sheath surface and an internal sheath surface that defines the central passage. When placed in the through hole, the insert is rotationally fixed relative to its longitudinal axis, but remains pivotally adjustable within the through hole relative to the osteosynthesis element.

35 Claims, 5 Drawing Sheets

(56) References Cited

U.S. PATENT DOCUMENTS 6,547,778 B1* 4/2003 Sklar et al. ............... 606/1
6,955,677 B2* 10/2005 Dahners ............... 606/287
2002/0016595 A1* 2/2002 Michelson ............... 606/73

FOREIGN PATENT DOCUMENTS

| TW | 463625 | 11/2001 |
| WO | 98/25534 | 6/1998 |
| WO | 03/055401 | 7/2003 |

* cited by examiner

DEVICE FOR OSTEOSYNTHESIS

RELATED APPLICATION DATA

The present application is a continuation of the U.S. National Stage designation of co-pending International Patent Application No. PCT/CH2002/000673, filed Dec. 6, 2002, the entire content of which is expressly incorporated herein by reference thereto.

FIELD OF THE INVENTION

The present invention relates to a device for osteosynthesis and, more particularly, to a device having a polyaxial insert for receiving a longitudinal bone fixation element, such as a bone screw, for securing the device to a bone.

BACKGROUND OF THE INVENTION

Devices of the present type are used for a polyaxial, rigid screw connection, particularly in the region of the spinal column, for example for pedicle screws or pedicle hooks. However, they can also be used generally for plate osteosynthesis. In addition, uses for external fixators as well as for intervertebral implants are also possible.

Such a device is already known from U.S. Pat. No. 6,235,003, in which a pivotable, ring-shaped insert is present between the screw head and the bore of the bone plate, which insert can be compressed and expanded by means of a slit, in order to thereby achieve improved fixation between screw and plate. The disadvantages of this known device are multiple. The axially rigid insert, configured to be circular, can turn with the screw as it is turned, and thereby prevents locking. Moreover, the insert can also twist completely within the plate bore, so that it then comes to rest with the wrong side up (inner cone narrows in the wrong direction).

The above discussion of the state of the art takes place merely to explain the surrounding field of the invention, and does not mean that the cited prior art was actually published or publicly known at the time of this application or its priority.

SUMMARY OF THE INVENTION

The present invention is intended to alleviate the problem discussed above. The invention is based on the problem of creating a device for osteosynthesis in which the longitudinal bone fixation elements (explained in greater detail in the following, using the example of bone screws) are polyaxially movable relative to the bone plate and can be locked at a stable angle, and which device requires a total of only four design elements, namely a bone plate, an insert for the hole in the plate, a longitudinal bone fixation element (e.g. bone screw), and a turning instrument (e.g. a screwdriver).

As compared with U.S. Pat. No. 6,235,033, the invention possesses the advantage that no additional spreading screw is required. It is also advantageous that the helical spring, which is axially compressible and expandable due to its nature, is also radially compressible and expandable, at the same time. Furthermore, production is simplified and less expensive. The helical spring furthermore has the advantage that when a bone screw is screwed in, the head of the bone screw, which is preferably configured to be conical, wedges itself into the interior of the helical spring.

In a preferred embodiment, the windings (preferably two or more windings) of the helical spring are configured to be non-round. In the following, "non-round" means any cross-section that deviates from a precisely round area, particularly prismatic and elliptical cross-sections. The cross-section of the passage that stands orthogonal to the central axis is also preferably configured to be non-round. In this connection, it is advantageous if the cross-section of the outer sheath surface that stands orthogonal to the longitudinal axis has a shape that essentially corresponds to the cross-section of the passage. In this way, the additional advantage can be achieved that the insert cannot rotate about its own axis while the bone screw is being screwed in. This is because the latter would have the result that no relative movement would take place between the insert and the screw any longer, so that spreading open of the insert would no longer be possible, and therefore locking of the screw would also not be possible.

Rotation-locking of the insert in the passage can be achieved not only by means of a corresponding geometry of the passage and the insert, but also with other means that have the result that the insert is mounted in the passage so as to prevent rotation relative to its longitudinal axis, as long as only the insert remains at least partially axially displaceable relative to the osteosynthesis element, and preferably pivotable, within the passage. For example, it is already sufficient if the helical spring is attached in the passage at least at one point of its spring helix (e.g. at one of its free ends).

In a particular embodiment, the cross-section of the passage in the osteosynthesis device preferably configured as a bone plate is configured to be polygonal, preferably hexagonal, so that the passage represents a prism, preferably a hexagonal prism. The helical spring then advantageously also has a polygonal (e.g. hexagonal) cross-section. In the hexagonal embodiment, the bone screw can be pivoted in three planes, at the same time, in the hexagonal passage, so that any desired pivot angle can be set. This is only limited by the plate thickness and by the contact of the insert with the narrowing in cross-section that is preferably made. In the case of most bone plates, of course, several passages are present.

In another embodiment, the passage of the osteosynthesis element widens at least in the direction of one of its two exit openings, preferably conically. The passage of the insert is typically configured prismatically, preferably as a hexagonal prism. However, it can also be configured as a hollow circular cylinder.

In another embodiment, the diameter of the central bore of the insert is narrowed in one direction, and the bore is preferably configured as a cone. This configuration allows spreading of the insert by means of a counter-cone, i.e. for example with a bone screw that has a conical screw head. However, the bore of the cylinder can also be configured as a circular cylinder.

The cross-section of the passage that stands orthogonal to the central axis, in the osteosynthesis device preferably configured as a bone plate, can also be configured to be elliptical.

It is practical if the surface of the insert is roughened, e.g. blasted to be rough, preferably in the region of its outer sheath curve. Accordingly, the passage in the bone plate can also be roughened, e.g. blasted to be rough. The passage can then be provided with a microtexture, in corresponding manner, e.g. in the form of grooves that run peripherally on the circumference. The advantage of this embodiment lies in the positive-lock connection between insert and bone plate that is achieved thereby.

The surface of the insert can be provided with a coating of a harder material than the insert, preferably in the region of its outer sheath curve, and possibly be additionally provided with a macrotexture. The passage of the osteosynthesis element can also be roughened up, preferably blasted to be rough. The passage of the osteosynthesis element can be provided with a coating of a harder material than that of the osteosynthesis element.

In another special embodiment, the passage in the osteosynthesis device, preferably configured as a bone plate, narrows towards the lower face and preferably also towards the upper face, so that a narrowing in cross-section results, which prevents the insert from falling out or being pressed out. It is practical, in this connection, if the cross-sectional narrowing of the passage and the compressibility of the insert are coordinated with one another, in such a manner that the insert, configured as a helical spring, can be introduced into the passage by means of a temporary reduction of its largest diameter.

In a particular embodiment, the outer sheath surface of the insert is convex, and the passage of the osteosynthesis element is configured to be concave.

It is advantageous if the osteosynthesis device, at least in the region of its passage, and the insert, at least in the region of its outer sheath curve, consist of different materials, preferably those having different hardness. The insert, for example, can consist of a biocompatible plastic, and the osteosynthesis device (e.g. a bone plate) can consist of a body-compatible metal. However, the insert can also be metallic, and the device can be made of a plastic, preferably a reinforced plastic. The different materials result in plastic deformation of the surface and therefore in a positive lock.

The height of the insert should be smaller, measured in the direction of its longitudinal axis, than the height of the passage in the bone plate, measured in the direction of its central axis. Advisably, the height of the insert range of 40%-85%, preferably 45% to 65% of the height of the passage.

The bone screws that serve for introduction into the insert preferably have a conical screw head, which additionally can be provided with an outside thread. The advantage of this configuration lies in the fact that spreading and locking of the insert in a single step is made possible.

In a particular embodiment, the diameter of the spring wire of the helical spring is smaller than or equal to the distance between two thread crests of the outside thread of the screw head. The cross-section of the spring wire of the helical spring can also be non-round, preferably square or diamond-shaped.

The pitch of the windings of the helical spring should advantageously correspond essentially to the pitch of the outside thread of the screw head. The diameter of the spring wire of the helical spring should furthermore advantageously be greater than the radial cross-sectional narrowing of the passage.

The invention and further developments of the invention will be explained in greater detail in the following, on the basis of the representations, some of them schematic, of several exemplary embodiments. Analogous applications for pedicle screws, pedicle hooks, external fixators, or intervertebral implants are possible.

BRIEF DESCRIPTION OF THE DRAWINGS

The present invention will be understood and appreciated more fully from the following detailed description, taken in conjunction with the drawings in which.

DETAILED DESCRIPTION OF THE PREFERRED EMBODIMENTS

Figure 1:
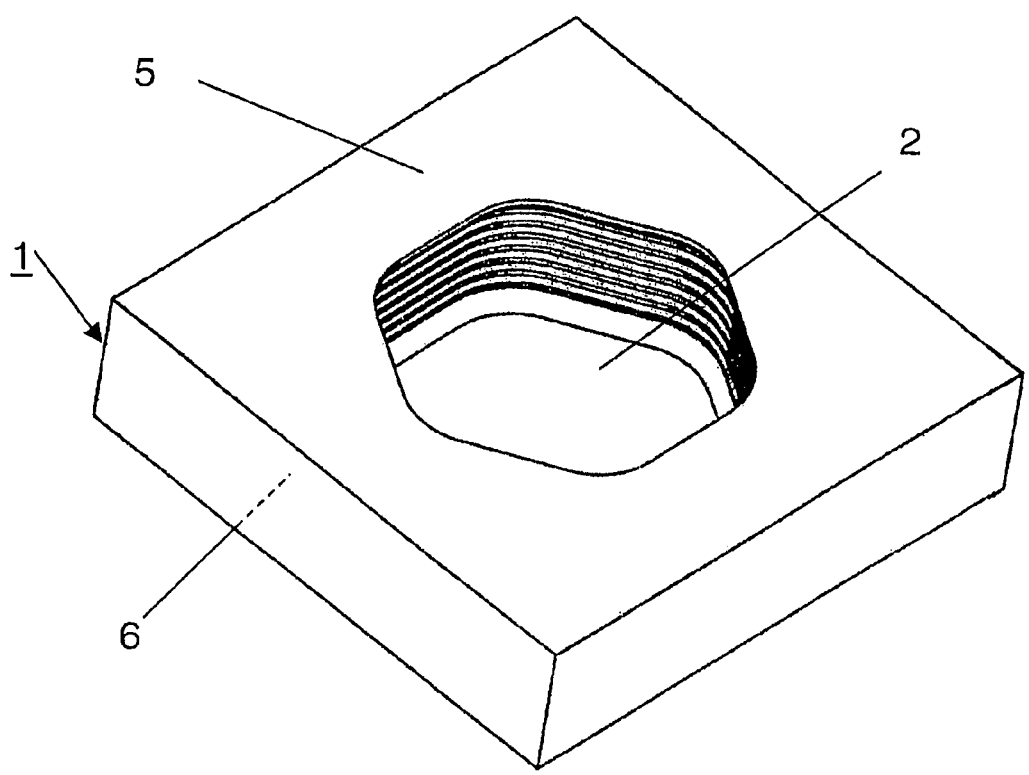
FIG. 1 shows a perspective representation of a device for osteosynthesis, implemented in the form of a bone plate.
Figure 2:
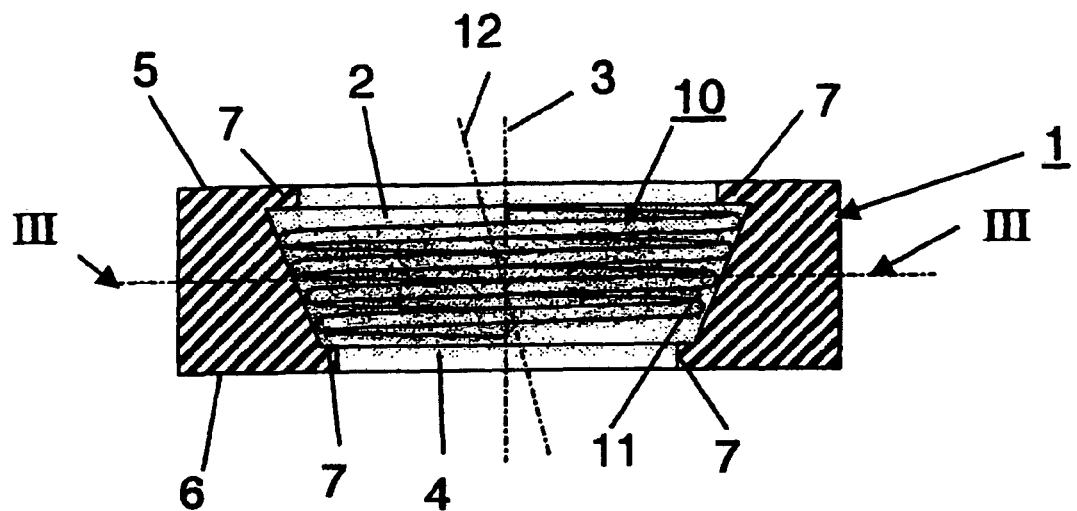
FIG. 2 shows a cross-section through the bone plate of FIG. 1, with an insert in the form of a helical spring.

The device for osteosynthesis shown in FIG. 1 to 5 consists of a bone plate 1 having a lower face 6 intended to rest against the bone, an upper face 5, as well as a passage 2 that connects the lower face 6 with the upper face 5, to accommodate a multi-axially pivotable insert 10 (FIGS. 2 and 4) for a bone screw 20 (FIG. 6), whereby the passage 2 has a central axis 3. The insert 10 that can be inserted into the passage 2 (FIGS. 2 and 4) possesses a central passage 11 for accommodating the bone screw 20 (FIG. 6), whereby the central passage 11 has a longitudinal axis 12, an outer sheath surface 13 that is intended for contact with the passage 2, and an inner sheath surface 14 that defines the central passage 11.

The insert 10 consists of a hexagonal helical spring, so that it is radially compressible and radially expandable. The passage 2 of the bone plate 1 has a radial narrowing 7 in cross-section towards the lower face 6 and also towards the upper face 5, in order to prevent the insert 10 from falling out or being pressed out. The narrowing 7 in cross-section of the passage 2 and the compressibility of the insert 10 are coordinated with one another in such a manner that the insert 10 can be introduced into the passage 2 in the compressed state.

As shown in FIG. 1, the passage 2 of the bone plate 1 is provided with a macrotexture in the form of grooves that run peripherally around the circumference.

Figure 3:
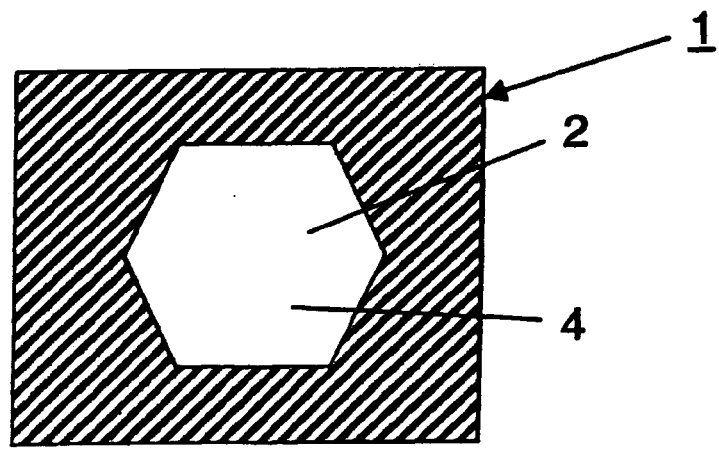
FIG. 3 shows a cross-section taken along the line III-III in FIG. 2.
Figure 4:
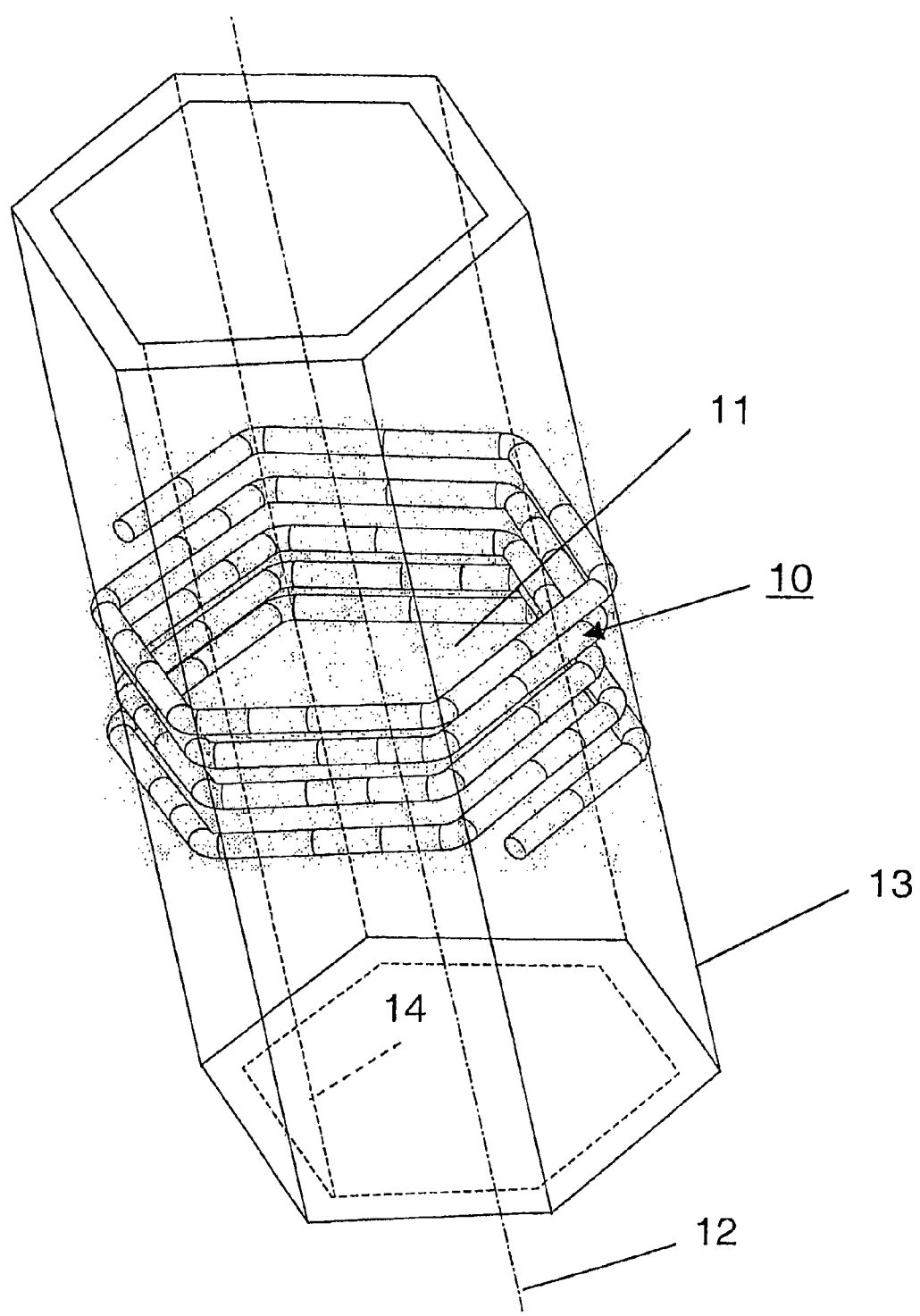
FIG. 4 shows a diagrammatic, perspective view of an insert in the form of a hexagonal helical spring.
Figure 5:
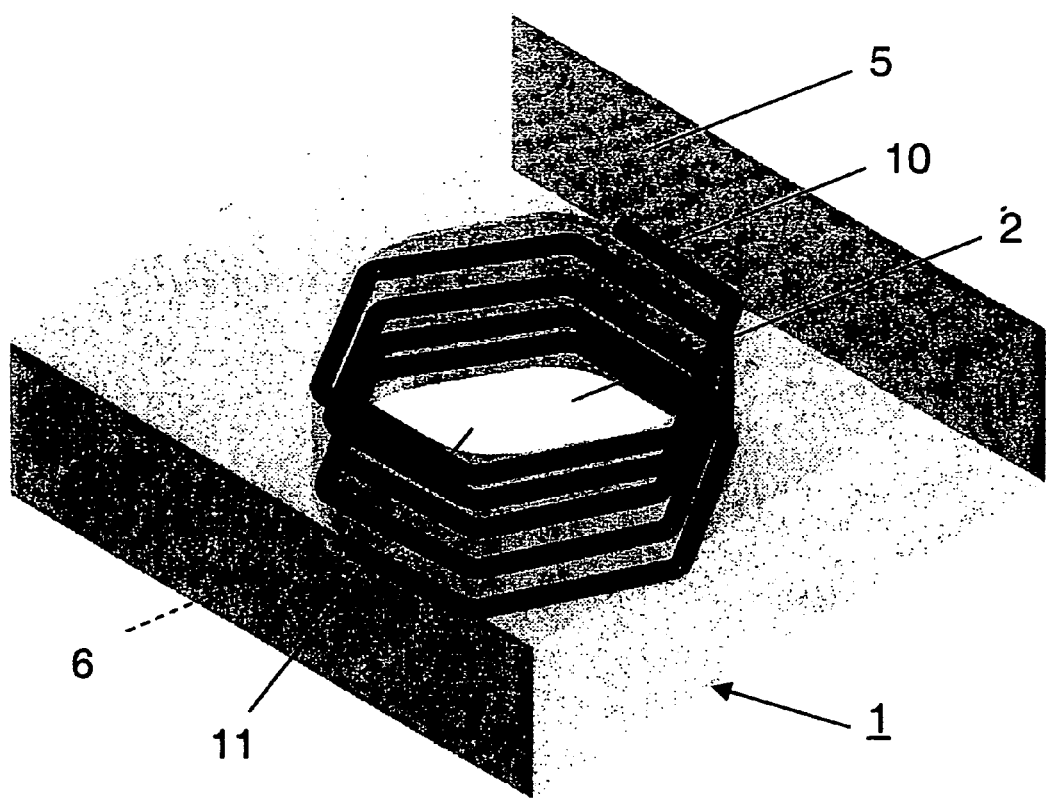
FIG. 5 shows a perspective representation of the bone plate of FIG. 1, with the insert shown in FIG. 4.

As shown in FIG. 3, the cross-section 4 of the passage 2, which stands orthogonal to the central axis 3, is approximately hexagonal, i.e. configured to be non-round. The cross-section of the insert 10, which stands orthogonal to the longitudinal axis 12, has a shape essentially corresponding to the cross-section 4 of the passage 2 of the bone plate 1, so that the insert 10 inserted in the passage 2 is fixed to prevent rotation relative to its longitudinal axis 12, but remains partially axially movable, i.e. pivotable, within the passage 2, relative to the bone plate 1.

As shown in FIG. 1, the diameter of the passage 4 narrows in the direction of the lower face 6 of the bone plate 1, so that the passage 4 is configured to be conical. Accordingly, the helical spring forming the insert 10 is also configured to be conical.

Figure 6:
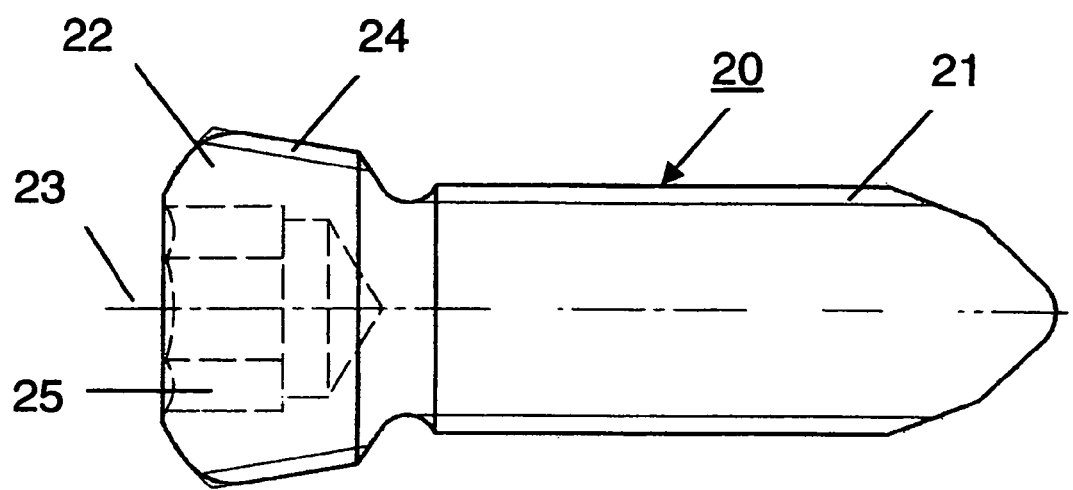
FIG. 6 shows a longitudinal section through a bone screw for the device for osteosynthesis.

The bone screw 20 shown in FIG. 6 can be inserted into the insert 10. The bone screw 20 possesses a threaded shaft 21 intended to be anchored in the bone, a screw axis 23, as well as a screw head 20 intended for insertion into the central passage 11 of the insert 10, which essentially corresponds to the shape of the central passage 11. The cross-section through the screw head 22, which stands orthogonal to the screw axis 23, is narrowed towards the threaded shaft 21, so that a cone results. The screw head 22 is provided with the outside thread 24, the pitch of which agrees with the pitch of the windings of the helical spring implemented as the insert 10. Furthermore, the screw head 22 possesses a hexagon socket 25 for accommodating an Allen wrench (not shown in the drawing).

In the following, the clinical use of the device for osteosynthesis will be described briefly.

The insert 10 of the device is already pre-mounted in the passage 2 of the bone plate 1 or in another osteosynthesis device. Insertion by the surgeon is therefore eliminated. The bone plate, with the inserts 10 pre-mounted in the passages 2, is placed onto the bone. This can be done either before or also after repositioning of various bone fragments or vertebrae. To set the bone screws 20, there are three standard scenarios:

a) drill, cut a thread, screw in;
b) drill, screw in (with self-tapping screws); or
c) screw in (with self-drilling and self-tapping screws).

The use of target bushings or drill bushings is also possible. Of course, the use of solid target bushings is not practical, because this would result in a loss of the advantage of a screw that can be adjusted in angle; however, such a target bushing could be useful in order to limit the angle of adjustability. Drill bushings are used if self-drilling screws are not used, and a hole has to be drilled first. In such a case, the drill bushing serves to protect soft tissue.

When several bone screws 20 are set, there are basically two possibilities: a) in the case that repositioning takes place before the bone plate is applied, the bone screws 20 can be fixed in place immediately; and b) in the case that repositioning takes place after the bone plate has been applied, the bone screws 20 are only screwed in so far, at first, that the bone plate is fixed in place on the bone; only then does final repositioning or correction take place, and the bone screws 20 can be locked in place by means of turning them several angle degrees further.

While the present invention has been described with reference to the preferred embodiments, those skilled in the art will recognize that numerous variations and modifications may be made without departing from the scope of the present invention. Accordingly, it should be clearly understood that the embodiments of the invention described above are not intended as limitations on the scope of the invention, which is defined only by the following claims.

The invention claimed is:

1. A device for holding a bone fixation element at a user selected angle, comprising:
   an osteosynthesis element having a bone fixation element receiving opening defining a central axis extending therethrough; and
   a helical spring insert sized and shaped to be mounted in the opening, a radial inner surface thereof defining an engaging surface for mounting a threaded head of a bone fixation element therein at any user selected angle relative to the central axis of the opening within a permitted range of angulation.

2. The device of claim 1, wherein the helical spring is non-round.

3. The device of claim 2 wherein the helical spring is prismatic.

4. The device of claim 1, wherein the opening in the osteosynthesis element has a non-round cross-section.

5. The device of claim 4, wherein the opening in the osteosynthesis element has a prismatic cross-section.

6. The device of claim 4, wherein a longitudinal cross-section of an outer surface of the helical spring has substantially the same shape as the cross-section of the opening through the osteosynthesis element.

7. The device of claim 1, wherein the helical spring is one of radially compressible and expandable.

8. The device of claim 1, wherein the insert is fixed in the opening to prevent rotation thereof relative to a longitudinal axis thereof and configured and adapted to remain partially axially movable within the opening relative to the osteosynthesis element.

9. The device of claim 1, wherein the cross-section of the opening in the osteosynthesis element is polygonal.

10. The device of claim 9, wherein the cross-section of the opening in the osteosynthesis element is hexagonal.

11. The device of claim 1, wherein the opening is generally prismatic.

12. The device of claim 1, wherein the opening through the osteosynthesis element conically widens in at least one direction along its central axis.

13. The device of claim 1, wherein a central passage of the insert conically widens in at least one direction along a longitudinal axis thereof.

14. The device of claim 1, wherein a central passage of the insert is generally prismatic.

15. The device of claim 1, wherein a shape of a central passage of the insert is generally cylindrical.

16. The device of claim 1, wherein at least one surface of the insert is roughened.

17. The device of claim 1, wherein at least one surface of the insert is coated with a harder material than the insert.

18. The device of claim 1, wherein the opening through the osteosynthesis element is roughened.

19. The device of claim 1, wherein the opening through the osteosynthesis element is provided with a coating of a harder material than that of the osteosynthesis element.

20. The device of claim 1, wherein the opening through the osteosynthesis element includes peripheral grooves that extend around a circumference of the opening.

21. The device of claim 1, wherein the opening through the osteosynthesis element narrows in cross-section at first and second ends thereof to maintain the insert therein.

22. The device of claim 1, wherein an outer surface of the insert is convex.

23. The device of claim 1, wherein the opening through the osteosynthesis element is concave.

24. The device of claim 1, wherein the osteosynthesis element and the insert are formed of different materials.

25. The device of claim 24, wherein the osteosynthesis element is formed of plastic and the insert is metallic.

26. The device of claim 1, wherein the insert has a height measured along its longitudinal axis that is smaller than a height of the opening through the osteosynthesis element measured in the direction of its central axis.

27. The device of claim 26, wherein the height of the insert ranges from 40% to 85% of the height of the opening.

28. The device of claim 1, further comprising a bone screw having a threaded shaft for engagement of bone and a threaded head sized and shaped for mounting in the central passage of the insert at an angle relative to the central axis thereof selected by a user.

29. The device of claim 1, wherein the osteosynthesis element is a bone plate.

30. The device of claim 1, wherein the osteosynthesis element is one of a pedicle screw and a pedicle hook.

31. The device of claim 1, wherein the osteosynthesis element is an external fixator.

32. The device of claim 1, wherein the osteosynthesis element is an intervertebral implant.

33. The device of claim 28, wherein a pitch of windings of the helical spring corresponds to a pitch of an outside thread of the screw head.

34. A device for holding a bone fixation element at a user selected angle, comprising:
   a bone plate having a bone fixation element receiving opening defining a central axis extending therethrough; and
   a helical spring insert sized and shaped to be mounted in the opening, a radial inner surface thereof defining an engaging surface for mounting a threaded head of a bone fixation element at any surgeon selected angle relative to the central axis of the opening within a permitted range of angulation, wherein the insert is configured and adapted to be secured against rotation relative to a longitudinal axis thereof while remaining pivotally adjustable relative to the central axis of the opening.

35. The device of claim 34, wherein a shape of the insert is substantially hexagonal.

\* \* \* \* \*